(12) United States Patent
Chopra et al.

(10) Patent No.: US 10,406,082 B2
(45) Date of Patent: Sep. 10, 2019

(54) ORAL CARE COMPOSITIONS

(75) Inventors: Suman Chopra, Monroe, NJ (US); Lin Fei, Kendall Park, NJ (US); Rahul Patel, Parsippany, NJ (US)

(73) Assignee: Colgate-Palmolive Company, New York, NY (US)

( * ) Notice: Subject to any disclaimer, the term of this patent is extended or adjusted under 35 U.S.C. 154(b) by 62 days.

(21) Appl. No.: 14/366,975

(22) PCT Filed: Dec. 21, 2011

(86) PCT No.: PCT/US2011/066485
§ 371 (c)(1),
(2), (4) Date: Jun. 19, 2014

(87) PCT Pub. No.: WO2013/095435
PCT Pub. Date: Jun. 27, 2013

(65) Prior Publication Data
US 2014/0348760 A1  Nov. 27, 2014

(51) Int. Cl.
*A61Q 11/00* (2006.01)
*A61K 8/21* (2006.01)
*A61K 8/25* (2006.01)
*A61K 8/81* (2006.01)

(52) U.S. Cl.
CPC ............. *A61K 8/25* (2013.01); *A61K 8/8164* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 3,535,421 A | 10/1970 | Briner et al. | |
| 3,538,230 A | 11/1970 | Pader et al. | |
| 3,678,154 A | 7/1972 | Widder et al. | |
| 3,862,307 A | 1/1975 | Di Diulio | |
| 3,937,807 A | 2/1976 | Haefele | |
| 3,959,458 A | 5/1976 | Agricola et al. | |
| 4,051,234 A | 9/1977 | Gieske et al. | |
| 4,340,583 A | 7/1982 | Wason | |
| 4,537,765 A * | 8/1985 | Gaffar ............... | A61Q 11/00 424/49 |
| 4,842,847 A | 6/1989 | Amjad | |
| 4,866,161 A | 9/1989 | Sikes et al. | |
| 4,885,155 A | 12/1989 | Parran et al. | |
| 4,992,258 A | 2/1991 | Mason | |
| 5,004,597 A | 4/1991 | Majeti et al. | |
| 5,188,821 A | 2/1993 | Gaffar et al. | |
| 5,192,531 A | 3/1993 | Gaffar et al. | |
| 5,240,697 A * | 8/1993 | Norfleet ............... | A61K 8/19 424/49 |
| 5,589,159 A | 12/1996 | Markowitz et al. | |
| 6,524,558 B2 | 2/2003 | Kleinberg et al. | |
| 2005/0031552 A1* | 2/2005 | Mori ................ | A61K 8/22 424/53 |
| 2005/0031553 A1 | 2/2005 | Mori et al. | |
| 2007/0253918 A1* | 11/2007 | Campanale ............. | A61K 8/21 424/53 |
| 2008/0267891 A1 | 10/2008 | Zaidel et al. | |
| 2010/0129307 A1 | 5/2010 | Singer et al. | |
| 2012/0276177 A1 | 11/2012 | Hilliard et al. | |

FOREIGN PATENT DOCUMENTS

| | | |
|---|---|---|
| RU | 2097021 | 11/1997 |
| RU | 2163798 | 3/2001 |
| WO | WO 2006/022849 | 3/2006 |
| WO | WO2010115041 | 10/2010 |
| WO | WO 2013/095435 | 6/2013 |

OTHER PUBLICATIONS

Anonyme: "Product Bulletin: Laponite DF" Rockwood Additives, Feb. 26, 2007, XP002683071, Retrieved from the Internet: URL:http://web.archive.org/web/20070226092530/http://www.rockwoodadditives.com/product_bulletins_eu/PB%20Laponite%20DF.pdf.

Anonyme: "Product Bulletin: Laponite XLG" Rockwood Additives, Feb. 26, 2007, XP002683072, Retrieved from the Internet: URL:http://web.archive.org/web/20070226092530/http://www.rockwoodadditives.com/product_bulletins_eu/PB%20Laponite%20XLG.pdf.

International Search Report and the Written Opinion issued in International Application PCT/US2011/066485 dated Sep. 28, 2012.

Written Opinion of the International Preliminary Examining Authority issued in International Application PCT/US2011/066485 dated Dec. 13, 2013.

English Translation of Official Action for RU Application No. 2010129762/15(047962).

XP002688376, http://online1.ispcorp.com/en-US/Pages/ProductDetail.aspx?BU=Ph, "Bantrez S-97 BF Solution", Search conducted Nov. 28, 2012.

* cited by examiner

*Primary Examiner* — Lezah Roberts

(57) ABSTRACT

Described herein are oral care compositions comprising (i) a magnesium alkali metal silicate complex clay, and (ii) an orally acceptable anionic polymer, in a dentifrice base, which compositions are useful for alleviating dental sensitivity. Also provided for, are methods of making and using the compositions described herein.

5 Claims, No Drawings

ORAL CARE COMPOSITIONS

CROSS-REFERENCE TO RELATED PATENT APPLICATIONS

The present application is a U.S. national stage entry under 35 U.S.C. § 371 of Patent Cooperation Treaty Patent Application No. PCT/US11/66485, filed Dec. 21, 2011, the entirety of which is incorporated herein by reference.

BACKGROUND

Tooth sensitivity is due to the exposure of dentin, the part of the tooth which covers the nerve, either through loss of the enamel layer or recession of the gums. The dentin contains a large numbers of microtubules that run from the outside of the tooth to the nerve in the center. When the dentin is exposed, the microtubules can transmit stimuli, e.g., from changes in temperature or from certain foods (acidic or sweet) to the nerve, causing the tooth or teeth to be painful. The pain usually subsides after a short period of time.

A number of treatments have been proposed for treatment and alleviation of dental hypersensitivity, including numbing the nerve with potassium ions (which reduces the membrane potential and ability of the neurons to transmit signals) or with topical anesthetics, or mechanical occlusion of the microtubules. However, despite the many products on the market and the many efforts to address this problem over the years, there still remains a need for safe and effective oral care products to address the problem of dental hypersensitivity.

SUMMARY

We have surprisingly discovered that a dentifrice comprising a combination of synthetic hectorite clay and an anionic polymer provides extremely good protection against transmission of signals via the dentinal microtubules, and is therefore effective to treat dental hypersensitivity.

Accordingly, the invention provides a dentifrice comprising a combination of a hectorite clay, e.g., laponite, and an orally acceptable anionic polymer, e.g. Gantrez, in a dentifrice base formulation, together with methods of making and using such compositions to reduce and treat dental hypersensitivity.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

The invention thus provides, in a first embodiment, a dentifrice composition (Composition 1) comprising (i) a magnesium alkali metal silicate complex clay, and (ii) an orally acceptable anioic polymer, in a dentifrice base; for example, 1.1. Composition 1 wherein the magnesium alkali metal silicate complex clay is a hectorite clay;

1.2. Composition 1.1 wherein the hectorite clay is a synthetic clay comprising 58-61% silicon dioxide, 26-29% magnesium oxide, 0.7-0.9% dilithium oxide and 2.6-3% disodium oxide, e.g., comprising about 59.5% of silicon dioxide, 27.5% magnesium oxide, 0.8% dilithium oxide and 2.8% disodium oxide;

1.3. Any of the foregoing compositions wherein the magnesium alkali metal silicate complex clay, when in dry form, comprises platelets having an average thickness of 0.8-1.2 nm, e.g., about 1 nm.

1.4. Any of the foregoing compositions wherein, following incorporation into the dentifrice, the clay remains substantially unhydrated.

1.5. Any of the foregoing compositions wherein the clay is about 0.2-5%, e.g., about 1 to 4%, or about 2.5% of the composition.

1.6. Any of the foregoing compositions wherein the anionic polymer is a synthetic anionic polymeric polycarboxylate.

1.7. Any of the foregoing compositions wherein the anionic polymer is a 1:4 to 4:1 copolymers of maleic anhydride or acid with another polymerizable ethylenically unsaturated monomer.

1.8. Any of the foregoing compositions wherein the anionic polymer is a methyl vinyl ether/maleic anhydride copolymer having an average molecular weight (M.W.) of about 30,000 to about 1,000,000, e.g. about 300,000 to about 800,000.

1.9. Any of the foregoing compositions wherein the anionic polymer is about 1-5, e.g., about 2% of the weight of the composition.

1.10. Any of the foregoing compositions further comprising an effective amount of fluoride, e.g., wherein the fluoride is a salt selected from stannous fluoride, sodium fluoride, potassium fluoride, sodium monofluorophosphate, sodium fluorosilicate, ammonium fluorosilicate, amine fluoride (e.g., N'-octadecyltrimethylendiamine-N,N,N'-tris(2-ethanol)-dihydrofluoride), ammonium fluoride, titanium fluoride, hexafluorosulfate, and combinations thereof 1.11. Any of the foregoing compositions comprising L-arginine in free or orally acceptable salt form.

1.12. Any of the foregoing compositions comprising buffering agents, e.g., sodium phosphate buffer (e.g., sodium phosphate monobasic and disodium phosphate)

1.13. Any of the foregoing compositions comprising a humectant, e.g., selected from glycerin, sorbitol, propylene glycol, polyethylene glycol, xylitol, and mixtures thereof 1.14. Any of the preceding compositions further comprising an abrasive or particulate;

1.15. The immediately preceding composition wherein the adhesive or particulate is selected from sodium bicarbonate, calcium phosphate (e.g., dicalcium phosphate dihydrate), calcium sulfate, precipitated calcium carbonate, silica (e.g., hydrated silica), iron oxide, aluminum oxide, perlite, plastic particles, e.g., polyethylene, and combinations thereof 1.16. Any of the preceding compositions comprising an abrasive in an amount of about 15 wt. % to about 70 wt. % of the total composition weight.

1.17. Any of the preceding compositions comprising one or more surfactants, e.g., selected from anionic, cationic, zwitterionic, and nonionic surfactants, and mixtures thereof, e.g., comprising an anionic surfactant, e.g., a surfactant selected from sodium lauryl sulfate, sodium ether lauryl sulfate, and mixtures thereof, e.g. in an amount of from about 0.3% to about 4.5% by weight.

1.18. Any of the preceding compositions further comprising a viscosity modifying amount of one or more polymers selected from polyethylene glycols, polysaccharides (e.g., cellulose derivatives, for example carboxymethyl cellulose, polysaccharide gums, for example xanthan gum or carrageenan gum), and combinations thereof 1.19. Any of the preceding compositions comprising gum strips or fragments.

1.20. Any of the preceding compositions further comprising flavoring, fragrance and/or coloring.

1.21. Any of the preceding compositions further comprising water.

1.22. Any of the foregoing compositions comprising one or more antibacterial agents, for example comprising an antibacterial agent selected from halogenated diphenyl ether (e.g. triclosan), herbal extracts and essential oils (e.g., rosemary extract, tea extract, magnolia extract, thymol, menthol, eucalyptol, geraniol, carvacrol, citral, hinokitol, catechol, methyl salicylate, epigallocatechin gallate, epigallocatechin, gallic acid, miswak extract, sea-buckthorn extract), bisguanide antiseptics (e.g., chlorhexidine, alexidine or octenidine), quaternary ammonium compounds (e.g., cetylpyridinium chloride (CPC), benzalkonium chloride, tetradecylpyridinium chloride (TPC), N-tetradecyl-4-ethylpyridinium chloride (TDEPC)), phenolic antiseptics, hexetidine, octenidine, sanguinarine, povidone iodine, delmopinol, salifluor, metal ions (e.g., zinc salts, for example, zinc citrate, stannous salts, copper salts, iron salts), sanguinarine, propolis and oxygenating agents (e.g., hydrogen peroxide, buffered sodium peroxyborate or peroxycarbonate), phthalic acid and its salts, monoperthalic acid and its salts and esters, ascorbyl stearate, oleoyl sarcosine, alkyl sulfate, dioctyl sulfosuccinate, salicylanilide, domiphen bromide, delmopinol, octapinol and other piperidino derivatives, nicin preparations, chlorite salts; and mixtures of any of the foregoing; e.g., comprising triclosan or cetylpyridinium chloride.

1.23. Any of the preceding compositions further comprising a whitening agent, e.g., a selected from the group consisting of peroxides, metal chlorites, perborates, percarbonates, peroxyacids, hypochlorites, and combinations thereof.

1.24. Any of the preceding compositions further comprising hydrogen peroxide or a hydrogen peroxide source, e.g., urea peroxide or a peroxide salt or complex (e.g., such as peroxyphosphate, peroxycarbonate, perborate, peroxysilicate, or persulphate salts; for example calcium peroxyphosphate, sodium perborate, sodium carbonate peroxide, sodium peroxyphosphate, and potassium persulfate);

1.25. Any of the preceding compositions further comprising an agent that interferes with or prevents bacterial attachment, e.g., solbrol or chitosan.

1.26. Any of the preceding compositions further comprising a source of calcium and phosphate selected from (i) calcium-glass complexes, e.g., calcium sodium phosphosilicates, and (ii) calcium-protein complexes, e.g., casein phosphopeptide-amorphous calcium phosphate 1.27. Any of the preceding compositions further comprising a soluble calcium salt, e.g., selected from calcium sulfate, calcium chloride, calcium nitrate, calcium acetate, calcium lactate, and combinations thereof 1.28. Any of the preceding compositions further comprising a physiologically or orally acceptable potassium salt, e.g., potassium nitrate or potassium chloride, in an amount effective to reduce dentinal sensitivity.

1.29. Any of the preceding compositions further comprising a breath freshener, fragrance or flavoring.

1.30. Any of the preceding compositions effective upon application to the oral cavity, e.g., with brushing, to (i) reduce hypersensitivity of the teeth, (ii) to reduce plaque accumulation, (iii) reduce or inhibit demineralization and promote remineralization of the teeth, (iv) inhibit microbial biofilm formation in the oral cavity, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; and/or (xv) promote systemic health, including cardiovascular health, e.g., by reducing potential for systemic infection via the oral tissues.

1.31. A composition obtained or obtainable by combining the ingredients as set forth in any of the preceding compositions.

1.32. Any of the preceding compositions in the form of a toothpaste.

1.33. Any of the preceding compositions further comprising effective amounts of additional agents selected from fluoride, 1-arginine in free or orally acceptable salt form, antibacterial agents in addition to the gallium salt and the basic amino acid polymer, anti-inflammatory compounds, and whitening agents.

1.34. Any of the preceding compositions wherein the composition is a toothpaste or mouthwash optionally further comprising one or more of one or more of water, abrasives, surfactants, foaming agents, vitamins, polymers, enzymes, humectants, thickeners, antimicrobial agents, preservatives, flavorings, colorings and/or combinations thereof 1.35. Any of the preceding compositions wherein the composition is toothpaste.

1.36. Any of the preceding compositions according comprising any, some or all the following ingredients by weight:

| Ingredient | Weight % |
| --- | --- |
| Water | 10-20, e.g. ca. 15 |
| Orally acceptable potassium salt, e.g., potassium nitrate | 3-7, e.g. ca. 5 |
| Noncaloric sweetener, e,g, sodium saccharin | 0-2, e.g. ca. 0.4 |
| Fluoride source, e.g., sodium monofluorophosphate | 0.5-1, e.g. ca. 0.76 |
| Humectant, e.g., glycerin, propylene glycol and combinations thereof | 40-60, e.g. ca. 50 |
| Thickeners, e.g. socium carboxymethyl cellulose, xanthan gum, and combinations thereof | 0.1-1, e.g., 0.7 |
| Pigment, e.g., titanium dioxide | 0-2, e.g. ca. 1 |
| Methyl vinyl ether/maleic anhydride polymer | 1-3, e.g. ca. 2 |
| Antiplaque agent, e.g. tetrasodium pyrophosphate | 0.5-2, e.g. ca. 1 |
| Base to adjust pH, e.g., sodium hydroxide 50% | 0-1, e.g. ca. 0.25 |
| Magnesium alkali metal silicate complex clay, e.g., synthetic hectorite | 0.2-5, e.g. ca. 2.5 |

-continued

| Ingredient | Weight % |
| --- | --- |
| Silica thickener | 2-6, e.g., ca. 4 |
| Anionic surfactant, e.g., sodium lauryl sulfate (SLS) | 1-3, e.g., ca. 1.5 |
| High cleaning silica | 2-10, e.g., ca. 5 |
| Silica abrasive | 5-15 e.g., ca. 10 |
| Flavor | 0-2, e.g., ca. 1 |

The invention further provides methods to (i) inhibit microbial biofilm formation in the oral cavity, (ii) to reduce plaque accumulation, (iii) reduce or inhibit demineralization and promote remineralization of the teeth, (iv) reduce hypersensitivity of the teeth, (v) reduce or inhibit gingivitis, (vi) promote healing of sores or cuts in the mouth, (vii) reduce levels of acid producing bacteria, (viii) to increase relative levels of non-cariogenic and/or non-plaque forming bacteria, (ix) reduce or inhibit formation of dental caries, (x), reduce, repair or inhibit pre-carious lesions of the enamel, e.g., as detected by quantitative light-induced fluorescence (QLF) or electrical caries measurement (ECM), (xi) treat, relieve or reduce dry mouth, (xii) clean the teeth and oral cavity, (xiii) reduce erosion, (xiv) whiten teeth; and/or (xv) promote systemic health, including cardiovascular health, e.g., by reducing potential for systemic infection via the oral tissues; comprising applying to the oral cavity, e.g., by brushing, a dentifrice comprising (i) a magnesium alkali metal silicate complex clay, and (ii) an orally acceptable anioic polymer; e.g., any of Composition 1, et seq.

The invention further provides the use of (i) a magnesium alkali metal silicate complex clay, and (ii) an orally acceptable anionic polymer, in combination in the manufacture of an oral care composition, e.g., any of Composition 1, et seq., e.g., for use in any of the methods as described in the preceding paragraph.

The invention further provides methods of manufacturing a dentifrice composition, e.g., Composition 1, et seq., comprising combining (i) a magnesium alkali metal silicate complex clay, and (ii) an orally acceptable anionic polymer, in a dentifrice base; together with an orally acceptable carrier. In a particular embodiment, the formulation is made as follows:

Clays:

Clays for use in the invention are magnesium alkali metal silicate complex clays. One such is hectorite, which is a smectite clay, belonging to a family of layered minerals that are comprised of very small individual platelets with a metal oxide center sandwiched between two silicone dioxide outer layers. Hectorite is a trioctahedral, magnesium based clay. It forms small, elongated disc-shaped particles, about 1 nm in thickness. Synthetic hectorite is a synthetic colloidal magnesium alkali metal silicate complex clay commercially available under the trade designation, Laponite®, e.g., from Southern Clay Products, Inc. Laponites are synthetic hectorite clays composed of magnesium, lithium, silica, oxygen, hydrogen, and sodium. Like natural hectorites, Laponites are composed in the dry state of platelets, about 1 nm thick, arranged in stacks. Each platelet has a double layer of tetrahedral silica bonded to oxygen atoms. Between the two silica layers there is a sheet of cations composed of magnesium and lithium in approximately a 5.3 to 0.7 ratio. These cations coordinate the inner row of silica bound oxygens and OH groups. In the presence of water, the cations create an osmotic gradient, causing the platelets to swell, forming a gel. Laponite® XLG is a product which have been processed to remove trace heavy metals and thus is particularly suitable for application in the instant invention. Laponite® XLG material contains 59.5% of silicon dioxide, 27.5% magnesium oxide, 0.8% dilithium oxide and 2.8% disodium oxide. It forms highly thixotropic gels when mixed in water.

In contrast to prior art suggesting the use of such clays as thickeners, in one aspect of this invention, following incorporation into the dentifrice, the clay remains substantially unhydrated, its primary purpose being to occlude the dentinal microtubules rather than to thicken the toothpaste. The clays are generally included in the dentifrice of the invention in amounts of from, e.g., 0.5-10%, e.g., 1-5%, e.g., about 2.5%.

Salt Forms:

The compositions of the invention are intended for topical use in the mouth, thus salts for use in the present invention should be orally acceptable, that is, safe for topical use in the mouth, in the amounts and concentrations provided. Suitable salts include salts known in the art to be pharmaceutically acceptable salts, which are generally considered to be orally acceptable for this purpose in the amounts and concentrations provided.

Active Agents:

The effective concentration of the active ingredients used herein will depend on the particular agent and the delivery system used. It is understood that a toothpaste for example will typically be diluted with water upon use, while a mouth rinse typically will not be. Thus, an effective concentration of active in a toothpaste will ordinarily be 5-15× higher than required for a mouth rinse. The concentration will also depend on the exact salt or polymer selected. For example, where the active agent is provided in salt form, the counterion will affect the weight of the salt, so that if the counterion is heavier, more salt by weight will be required to provide the same concentration of active ion in the final product. Arginine, where present, may be present at levels from, e.g., about 0.1 to about 20 wt % (expressed as weight of free base), e.g., about 0.1 to about 3 wt % for a mouthrinse, about 1 to about 10 wt % for a consumer toothpaste or about 7 to about 20 wt % for a professional or prescription treatment product. Fluoride where present may be present at levels of, e.g., about 25 to about 25,000 ppm, for example about 25 to about 250 ppm for a mouthrinse, about 750 to about 2,000 ppm for a consumer toothpaste, or about 2,000 to about 25,000 ppm for a professional or prescription treatment product. Levels of antibacterial agents in addition to the gallium salt and basic amino acid polymer will vary similarly, with levels used in toothpaste being e.g., about 5 to about 15 times greater than used in mouthrinse. For example, a triclosan mouthrinse may contain, e.g., about 0.03 wt % triclosan while a triclosan toothpaste may contain about 0.3 wt % triclosan.

Fluoride Ion Source:

The oral care compositions may further include one or more fluoride ion sources, e.g., soluble fluoride salts. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, sodium monofluorophosphate as well as mixtures thereof. In certain embodiments, the oral care composition of the invention may also contain a source of fluoride ions or fluorine-providing ingredient in amounts sufficient to supply about 25 ppm to about 25,000 ppm of fluoride ions, generally at least about 500 ppm, e.g., about 500 to about 2000 ppm, e.g., about 1000 to about 1600 ppm, e.g., about 1450 ppm. The appropriate level of fluoride will depend on the particular application. A toothpaste for general consumer use would typically have about 1000 to about 1500 ppm, with pediatric toothpaste having somewhat less. A dentifrice or coating for professional application could have as much as about 5,000 or even about 25,000 ppm fluoride. Fluoride ion sources may be added to the compositions of the invention at a level of about 0.01 wt. % to about 10 wt. % in one embodiment or about 0.03 wt. % to about 5 wt. %, and in another embodiment about 0.1 wt. % to about 1 wt. % by weight of the composition in another embodiment. Weights of fluoride salts to provide the appropriate level of fluoride ion will obviously vary based on the weight of the counter ion in the salt.

Abrasives:

The compositions of the invention, e.g. Composition 1 et seq. may comprise a calcium phosphate abrasive, e.g., tricalcium phosphate ($Ca_3(PO_4)_2$), hydroxyapatite ($Ca_{10}(PO_4)_6(OH)_2$), or dicalcium phosphate dihydrate ($CaHPO_4.2H_2O$, also sometimes referred to herein as DiCal) or calcium pyrophosphate. The compositions may include one or more additional abrasives, for example silica abrasives such as precipitated silicas having a mean particle size of up to about 20 microns, such as Zeodent 115®, marketed by J. M. Huber. Other useful abrasives also include sodium metaphosphate, potassium metaphosphate, aluminum silicate, calcined alumina, bentonite or other siliceous materials, or combinations thereof. The silica abrasive polishing materials useful herein, as well as the other abrasives, generally have an average particle size ranging between about 0.1 and about 30 microns, about between 5 and about 15 microns. The silica abrasives can be from precipitated silica or silica gels, such as the silica xerogels described in U.S. Pat. No. 3,538,230, to Pader et al. and U.S. Pat. No. 3,862,307, to Digiulio, both incorporated herein by reference. Particular silica xerogels are marketed under the trade name Syloid® by the W. R. Grace & Co., Davison Chemical Division. The precipitated silica materials include those marketed by the J. M. Huber Corp. under the trade name Zeodent®, including the silica carrying the designation Zeodent 115 and 119. These silica abrasives are described in U.S. Pat. No. 4,340,583, to Wason, incorporated herein by reference. In certain embodiments, abrasive materials useful in the practice of the oral care compositions in accordance with the invention include silica gels and precipitated amorphous silica having an oil absorption value of less than about 100 cc/100 g silica and in the range of about 45 cc/100 g to about 70 cc/100 g silica. Oil absorption values are measured using the ASTA Rub-Out Method D281. In certain embodiments, the silicas are colloidal particles having an average particle size of about 3 microns to about 12 microns, and about 5 to about 10 microns. Low oil absorption silica abrasives particularly useful in the practice of the invention are marketed under the trade designation Sylodent XWA® by Davison Chemical Division of W.R. Grace & Co., Baltimore, Md. 21203. Sylodent 650 XWA®, a silica hydrogel composed of particles of colloidal silica having a water content of 29% by weight averaging about 7 to about 10 microns in diameter, and an oil absorption of less than about 70 cc/100 g of silica is an example of a low oil absorption silica abrasive useful in the practice of the present invention.

The abrasive is present in the oral care composition of the present invention at a concentration of about 10 to about 60% by weight, in other embodiment about 20 to about 45% by weight, and in another embodiment about 30 to about 50% by weight.

The oral care compositions of the invention also may include an agent to increase the amount of foam that is produced when the oral cavity is brushed. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of about 200,000 to about 7,000,000. In one embodiment the molecular weight will be about 600,000 to about 2,000,000 and in another embodiment about 800,000 to about 1,000,000. Polyox® is the trade name for the high molecular weight polyoxyethylene produced by Union Carbide. The polyoxyethylene may be present in an amount of about 1% to about 90%, in one embodiment about 5% to about 50% and in another embodiment about 10% to about 20% by weight of the oral care carrier component of the oral care compositions of the present invention. The dosage of foaming agent in the oral care composition (i.e., a single dose) is about 0.01 to about 0.9% by weight, about 0.05 to about 0.5% by weight, and in another embodiment about 0.1 to about 0.2% by weight.

Surfactants:

The compositions useful in the invention may contain anionic surfactants, for example:

i. water-soluble salts of higher fatty acid monoglyceride monosulfates, such as the sodium salt of the monosulfated monoglyceride of hydrogenated coconut oil fatty acids such as sodium N-methyl N-cocoyl taurate, sodium cocomonoglyceride sulfate, ii. higher alkyl sulfates, such as sodium lauryl sulfate, iii. higher alkyl-ether sulfates, e.g., of formula CH3(CH2)mCH2(OCH2CH2)nOSO3X, wherein m is 6-16, e.g., 10, n is 1-6, e.g., 2, 3 or 4, and X is Na or K, for example sodium laureth-2 sulfate (CH3(CH2)10CH2(OCH2CH2)2OSO3Na).

iv. higher alkyl aryl sulfonates such as sodium dodecyl benzene sulfonate (sodium lauryl benzene sulfonate)

v. higher alkyl sulfoacetates, such as sodium lauryl sulfoacetate (dodecyl sodium sulfoacetate), higher fatty acid esters of 1,2 dihydroxy propane sulfonate, sulfocolaurate (N-2-ethyl laurate potassium sulfoacetamide) and sodium lauryl sarcosinate.

By "higher alkyl" is meant, e.g., C6-30 alkyl. In particular embodiments, the anionic surfactant is selected from sodium lauryl sulfate and sodium ether lauryl sulfate. The anionic surfactant may be present in an amount which is effective, e.g., >0.01% by weight of the formulation, but not at a concentration which would be irritating to the oral tissue, e.g., <10%, and optimal concentrations depend on the particular formulation and the particular surfactant. For example, concentrations used or a mouthwash are typically on the order of one tenth that used for a toothpaste. In one embodiment, the anionic surfactant is present in a toothpaste at from about 0.3% to about 4.5% by weight, e.g., about 1.5%. The compositions of the invention may optionally contain mixtures of surfactants, e.g., comprising anionic surfactants and other surfactants that may be anionic, cationic, zwitterionic or nonionic. Generally, surfactants are those which are reasonably stable throughout a wide pH range. Surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. In certain embodiments, the anionic surfactants useful herein include the water-soluble salts of alkyl sulfates having about 10 to about 18 carbon atoms in the alkyl radical and the water-soluble salts of sulfonated monoglycerides of fatty acids having about 10 to about 18 carbon atoms. Sodium lauryl sulfate, sodium lauroyl sarcosinate and sodium coconut monoglyceride sulfonates are examples of anionic surfactants of this type. In a particular embodiment, the composition of the invention, e.g., Composition 1, et seq., comprises sodium lauryl sulfate.

The surfactant or mixtures of compatible surfactants can be present in the compositions of the present invention in about 0.1% to about 5.0%, in another embodiment about 0.3% to about 3.0% and in another embodiment about 0.5% to about 2.0% by weight of the total composition.

Flavoring Agents:

The oral care compositions of the invention may also include a flavoring agent. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent may be incorporated in the oral composition at a concentration of about 0.1 to about 5% by weight and about 0.5 to about 1.5% by weight. The dosage of flavoring agent in the individual oral care composition dosage (i.e., a single dose) is about 0.001 to 0.05% by weight and in another embodiment about 0.005 to about 0.015% by weight.

Polymers:

The oral care compositions of the invention also include one or more anionic polymers to enhance the effect of the clay, and also may include additional polymers to adjust the viscosity of the formulation or enhance the solubility of other ingredients. Such additional polymers include polyethylene glycols, polysaccharides (e.g., cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g., potassium and sodium) or ammonium salts.

The compositions of the invention include an anionic polymer to enhance the effect of the clay, for example in an amount of from about 0.05 to about 5%. Such agents are known generally for use in dentifrice, although not for this particular application, useful in the present invention are disclosed in U.S. Pat. Nos. 5,188,821 and 5,192,531; and include synthetic anionic polymeric polycarboxylates, such as 1:4 to 4:1 copolymers of maleic anhydride or acid with another polymerizable ethylenically unsaturated monomer, preferably methyl vinyl ether/maleic anhydride having a molecular weight (M.W.) of about 30,000 to about 1,000,000, most preferably about 300,000 to about 800,000. These copolymers are available for example as Gantrez. e.g., AN 139 (M.W. 500,000), AN 119 (M.W. 250,000) and preferably S-97 Pharmaceutical Grade (M.W. 700,000) available from ISP Technologies, Inc., Bound Brook, N.J. 08805. The enhancing agents when present are present in amounts ranging from about 0.05 to about 3% by weight. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of about 1,000 to about 2,000,000, described in U.S. Pat. No. 4,842,847, Jun. 27, 1989 to Zahid, incorporated herein by reference. Another useful class of polymeric agents includes polyamino acids containing proportions of anionic surface-active amino acids such as aspartic acid, glutamic acid and phosphoserine, (in addition to the basic amino acid polymers), e.g. as disclosed in U.S. Pat. No. 4,866,161 Sikes et al., incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of about 0.5% to about 5.0% by weight of the total composition are used.

Water:

Water may also be present in the oral compositions of the invention. Water, employed in the preparation of commercial oral compositions should be deionized and free of organic impurities. Water commonly makes up the balance of the compositions and includes about 0.1% to about 90%, about 10% to about 80% or about 20% to about 70%, or about 30% to about 60% by weight of the oral compositions. This amount of water includes the free water which is added plus that amount which is introduced with other materials such as with sorbitol or any components of the invention.

Humectants:

Within certain embodiments of the oral compositions, it is also desirable to incorporate a humectant to prevent the composition from hardening upon exposure to air. Certain humectants can also impart desirable sweetness or flavor to dentifrice compositions. The humectant, on a pure humectant basis, generally includes about 15% to about 70% in one embodiment or about 30% to about 65% in another embodiment by weight of the dentifrice composition. Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

Other Optional Ingredients:

In addition to the above-described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele, all being incorporated herein by reference.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

Dentifrice Comprising Magnesium Alkali Metal Silicate Complex Clay and Anionic Polymer Laponite XLG (Rockwood Additive Limited Company) is successfully incorporated in a silica dentifrice. The laponite is added with the silica, to ensure that the laponite remains substantially unhydrated, which is necessary for its occlusive activity. Prototype dentifrice formulations are as follows:

TABLE 1

| Comp. Ex. III | |
| --- | --- |
| Ingredient | Weight % |
| Deionized Water | 15 |
| Potassium Nitrate | 5 |
| Sodium Saccharin | 0.4 |
| Sodium Monofluorophosphate | 0.76 |
| Veg Glycerin | 46.79 |
| Propylene Glycol | 5 |
| Sodium CMC | 0.5 |
| Xanthan | 0.2 |

TABLE 1-continued

| Comp. Ex. III | |
| --- | --- |
| Ingredient | Weight % |
| Titanium Dioxide | 1 |
| Tetrasodium Pyrophosphate | 1 |
| Sodium Hydroxide 50% | 0.25 |
| Laponite XLG | 2.5 |
| Silica Thickener | 4.00 |
| Sodium lauryl sulfate (SLS) | 1.50 |
| High Cleaning Silica | 5.00 |
| Silica Abrasive | 10.00 |
| Flavor | 1.10 |

TABLE 2

| Formula 1 | |
| --- | --- |
| Ingredient | Weight % |
| Deionized Water | 15 |
| Potassium Nitrate | 5 |
| Sodium Saccharin | 0.4 |
| Sodium Monofluorophosphate | 0.76 |
| Veg Glycerin | 45.29 |
| Propylene Glycol | 5 |
| Sodium CMC | 0.5 |
| Xanthan | 0.2 |
| Titanium Dioxide | 1 |
| Gantrez | 2 |
| Tetrasodium Pyrophosphate | 1 |
| Sodium Hydroxide 50% | 0.25 |
| Laponite XLG | 2.5 |
| Silica Thickener | 4 |
| Sodium lauryl sulfate (SLS) | 1.5 |
| High Cleaning Silica | 5 |
| Silica Abrasive | 10 |
| Flavor | 1.1 |

Example 2

The effectiveness of an exemplary composition of the present invention (Formula 1) is compared to formulations which do not contain the inventive combinations described herein, for their ability to occlude the dentinal tubules. Tubule occlusion is measured using hydraulic conductance. Human dentin segments are cut from extracted molars, mounted on acrylic blocks, etched and connected to a Flodec to measure hydraulic conductance. Segments are treated (1 min) with a composition of the present invention (Formula 1—a magnesium alkali metal silicate complex clay+an orally acceptable anionic polymer), a conventional silica containing composition (Comp. Ex. I—negative control), a strontium containing composition (Comp. Ex. II—positive control), and a laponite containing composition (Comp. Ex. III—positive control). The blocks are rinsed, connected to the Flodec, and the conductance is measured. Blocks are rinsed again and incubated in PBS for at least 2 hours before the next treatment. The cycle is repeated for a total of 2 treatments. After second treatment, the blocks are incubated in PBS for overnight and conductance is measured. The segments are challenged for 1-minute with 6% citric-acid and conductance is measured again, and the percentage of reduction in fluid flow after each treatment and acid challenge is recorded.

The data described in Table 4 (below) demonstrates that the compositions of the present invention occlude dentine tubules to a significantly greater extent than compositions which do not contain the inventive combinations described herein.

TABLE 4

|  | Treatment 1 | Treatment 2 | Overnight reading | Acid challenge |
|---|---|---|---|---|
| Comp. Ex. I | 30.26 | 26.82 | 31.74 | 18.19 |
| Comp. Ex. II | 26.64 | 44.34 | 40.09 | 19.42 |
| Comp. Ex. III | 73.53 | 68.43 | 58.83 | 62.54 |
| Formula 1 | 91.78 | 91.63 | 85.94 | 86.58 |

The invention claimed is:

1. A dentifrice composition comprising, (all percentages are by weight and based upon the total weight of the dentifrice composition):
   (i) 1-5% of a hectorite clay blended in 10 to 60% silica abrasive; and
   (ii) a dentifrice base comprising 10 to 20% water, and 1-5% of an orally acceptable anionic polymer, and 40 to 60% of humectant selected from glycerin, propylene glycol and combinations thereof,
      wherein the anionic polymer is a methyl vinyl ether/maleic anhydride copolymer;
      wherein the composition further comprises an effective amount of a fluoride salt selected from the group consisting of stannous fluoride, sodium fluoride, potassium fluoride, sodium monofluorophosphate or a mixture thereof; and an effective amount of potassium nitrate or potassium chloride; and
      wherein the hectorite clay is a synthetic clay comprising 58-61% silicon dioxide, 26-29% magnesium oxide, 0.7-0.9% dilithium oxide and 2.6-3% disodium oxide.

2. The composition of claim 1, wherein the methyl vinyl ether/maleic anhydride copolymer has an average molecular weight of about 30,000 to about 100,000.

3. The composition according to claim 1 further comprising an effective amount of an additional agent selected from arginine in free or orally acceptable salt form, an anti-inflammatory agent, a whitening agent, and a combination of two or more thereof.

4. The composition according to claim 1 wherein the composition is a toothpaste comprising one or more of water, an abrasive, a surfactant, a foaming agent, a vitamin, a polymer, an enzyme, a humectant, a thickener, an antimicrobial agent, a preservative, a flavoring, a coloring and/or a combination of two or more thereof.

5. A method for treating or preventing dental hypersensitivity comprising administering an effective amount of a composition according to claim 1 to the oral cavity of a subject in need thereof.

* * * * *